United States Patent [19]

Riccardo et al.

[11] Patent Number: 5,026,843
[45] Date of Patent: Jun. 25, 1991

[54] PROCESS FOR THE PREPARATION OF CEFTRIAXONE

[75] Inventors: Monguzzi Riccardo, Monza; Menaspace Silvano, Rho; Anzaghi Piergiorgio, San Colombano Al Lambro, all of Italy

[73] Assignee: S.B.D. Synthetic and Biological Dvlpmnts. S.r.l., S. Giuliano, Italy

[21] Appl. No.: 416,627

[22] Filed: Oct. 3, 1989

[30] Foreign Application Priority Data

May 23, 1989 [IT]  Italy ............................... 20612 A/89

[51] Int. Cl.$^5$ .................. C07D 501/36; A61K 31/545
[52] U.S. Cl. .................................................... 540/227
[58] Field of Search ................ 514/206; 540/227, 226, 540/221

[56] References Cited

FOREIGN PATENT DOCUMENTS 1177823  11/1984  Canada .

Primary Examiner—Nicholas S. Rizzo
Attorney, Agent, or Firm—Armstrong, Nikaido, Marmelstein, Kubovcik & Murray

[57] ABSTRACT

An improved process for the preparation of an antibiotic substance, more specifically 7{[2-(2-aminothiazol-4-yl)-2-synmethoxyimino]acetamido}-3-{[(2,5-dihydro-6-hydroxy-2-methyl-5-oxo-1,2,4-triazin-3-yl)thio]methyl}-3-cephem-4-carboxylic acid in the form of disodium salt hemieptahydrate is described, where 7-amino-3-{[(2,5-dihydro-6-hydroxy-2-methyl-5-oxo-1,2,4-triazin-3-yl)thio]methyl}-3-cephem-4-carboxylic acid is made to react with 2-mercaptobenzothiazole 2-(2-aminothiazol-4-yl)-2-syn-methoxyiminoacetate in an aqueous solution in suitable solvents, in the presence of an amine selected from the group consisting of trimethylamine, triethylamine, 1,4-dimethylpiperazine, N-ethylpiperidine, pyridine and dimethylaminopyridine and the obtained aqueous solution is treated with a base selected from the group consisting of dicyclohexylamine, diphenylamine, diisopropylamine, N-tert-butylcyclohexylamine and N,N-dibenzylethylendiamine, in a suitable form, and the thus formed precipitate is reacted in suitable solvents with sodium 2-ethylhexanoate to give the desired compound.

3 Claims, No Drawings

PROCESS FOR THE PREPARATION OF CEFTRIAXONE

The invention relates to an improved process for the preparation of an antibiotic substance belonging to the cephalosporin group, more specifically, for the production of 7-{[2-(2-aminothiazol-4-yl)-2-syn-methoxyimino]acetamido}-3-{[(2,5-dihydro-6-hydroxy-2-methyl-5-oxo-1,2,4-triazin-3-yl)thio]methyl}-3-cephem-4-carboxylic acid disodium salt hemiheptahydrate or ceftriaxone disodium salt hemiheptahydrate.

Ceftriaxone is a cephalisporin of a great therapeutical interest due to its effective antibacterial activity; therefore administered as disodium salt hemiheptahydrate it finds application in the treatment of several affections.

Ceftriaxone is prepared by first introducing the suitable substituent into position 3 of the cephalosporanic nucleus, then introducing the suitable substituent to the nitrogen in position 7. Alternatively, the radical substituent to the nitrogen atom in position 7 may first be introduced and then the substituent to the methylene in position 3.

Some processes for the preparation of ceftriaxone are known; among them the European Patent Application 0 037 380 in the name of Biochemie GmbH describes a preparation which starts from 7-amino-3-(2,5-dihydro-6-hydroxy-2-methyl-5-oxo-1,2,4-triazin-3-yl)thiomethyl-3-cephem-4-carboxylic acid, which suitably protected at the carboxylic group, is made to react with 2-mercaptobenzothiazole 2-(2-aminothiazol-4-yl)-2-syn-methoxymino acetate, then, after being deprotected, it gives ceftriaxone in the form of free acid. Its corresponding transformation in its soluble form as disodium salt is carried out afterwards according to the known techniques.

It has now been found, and it constitutes the object of the present invention, that the reaction between 7-amino-3-(2,5-dihydro-6-hydroxy-2-methyl-5-oxo-1,2,4-triazin-3-yl)thiomethyl-3-cephem-4-carboxylic acid and 2-mercaptobenzothiazole 2-(2-aminothiazol-4-yl)-2-syn-methoxyiminoacetate may also be carried out in the presence of particular reagents and solvents which allow the reaction to be performed in extremely mild ambient conditions and do not require the use of specific protecting groups to the carboxy radical in position 4 of the cephalosporanic nucleus. The use of the reagents and solvents in the process of the invention makes it possible to obtain ceftriaxone disodium salt hemiheptahydrate in a very pure form and with very high total yields, which are always higher than 85%.

The process of the invention may be schematically represented as follows:

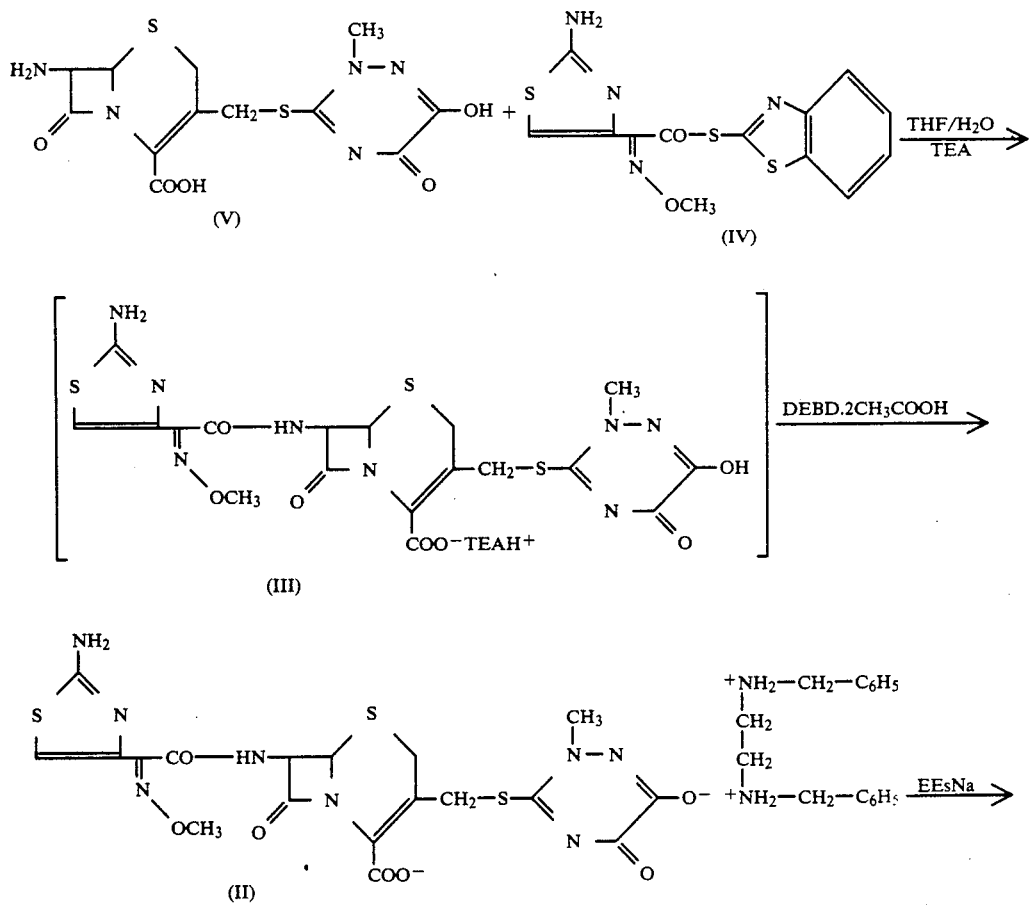

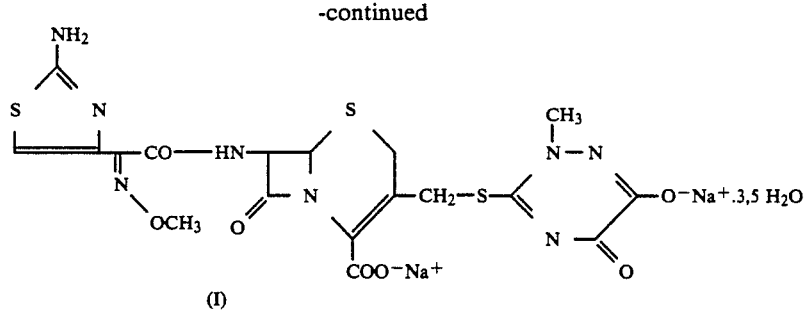

(I)

The reaction (a) is carried out in an aqueous solution at a temperature of from −20° to 30° C., preferably of from −5° to 25° C. and more preferably between 0° and 10° C., in the presence of suitable organic solvents such as, for example, tetrahydofuran, dimethylacetamide, dimethylformamide, dioxane, dimethoxyethane or suitable mixtures thereof, preferably in the presence of tetrahydrofuran/dimethylacetamide. As an alternative to triethylamine, reaction (a) may be performed in the presence of different amines such as, for example, trimethylamine, 1,4-dimethylpiperazine, N-ethylpiperidine, pyridine and dimethylaminopyridine.

The so formed salt (III) is not isolated from the aqueous solution which contains it, but, and this is of a high interest as to economy of the process, the aqueous solution is directly treated with N,N-dibenzylethylenediamine diacetate and obtaining therefrom a practically quantitative precipitation of the salt (II) in a pure state.

As an alternative to N,N-dibenzylethylenediamine, other suitable bases such as, for example, dicyclohexylamine, diphenylamine, diisopropylamine and N-tert-butylcyclohexylamine may be used in reaction (b).

The salt (II) is a new compound which, in itself, shows to possess antibacterial activity.

The salt (II) is then made to react in the presence of suitable organic solvents such as, for example, methylethylketone, acetone and methylisobutylketone or alcohols such methyl or ethyl alcohol, with sodium 2-ethylhexanoate to give ceftriaxone disodium salt hemiheptahydrate in a pure state, with yields, which referred to the whole process, are always higher than 85%.

The following Example is given to illustrate in a better manner the invention without limiting it.

EXAMPLE

7-{[2-(2-aminothiazol-4-yl)-2-syn-methoxyimino]acetamido}-3-{[(2,5-dihydro-6-hydroxy-2-methyl-5-oxo-1,2,4-triazin-3-yl)thio]methyl}-3-cephem-4-carboxylic acid disodium salt hemiheptahydrate To a solution consisting of 15 ml dimethylacetamide, 100 ml tetrahydrofuran and 100 ml water, 10 g 7-amino-3-{[(2,5-dihydro-6-hydroxy-2-methyl-5-oxo-1,2,4-triazin-3-yl)thio]methyl}-3-cephem-4-carboxylic acid and 11.32 g 2-mercaptobenzothiazole 2-(2-aminothiazol-4-yl)-2-syn-methoxyimino acetate are added at the temperature of 3° C. The mixture is kept at 3° C. and, under stirring, 6.53 ml triethylamine are added, dropwise, thereto. To the obtained clear solution are added 100 ml ethyl acetate; it is stirred, settled, the aqueous phase separated and 10 g N,N-dibenzylethylenediamine diacetate added thereto under stirring. To the reaction mixture, kept under stirring, are then added 75 ml methylene chloride and a precipitate is separated which, dried under vacuo, gives 20.5 g N,N-dibenzylethylenediamine 7-{[2-(2-aminothiazol-4-yl)-2-syn-methoxyimino]acetamido}-3-{[(2,5-dihydro-6-hydroxy-2-methyl-5-oxo-1,2,4-triazin-3-yl)thio]methyl}-3-cephem-4-carboxylate melting at 234°-248° C. (with decomposition); IR (Nujol, cm$^{-1}$): 1770 lactam —C=0. Yield 97.62%.

Grams 20.5 N,N-dibenzylethylenediamine 7-{[2-(2-aminothiazo-4-yl)-2-syn-methoxyimino]acetamido}-3-{[(2,5-dihydro-6-hydroxy-2-methyl-5-oxo-1,2,4-triazin-3-yl)thio]methyl}-3-cephem-4-carboxylate are treated with a solution formed by 50 ml water and 360 ml acetone, then with a solution consisting of 9.85 g sodium 2-ethylhexanoate in 100 ml acetone. The precipitate is separated by filtration, washed three times with 50 ml acetone each time and dried under vacuo to give 15.15 g 7-{[2-(2-aminothiazol-4-yl)-2-syn-methoxyimino]acetamido}-3-{[(2,5-dihydro-6-hydroxy-2-methyl-5-oxo-1,2,4-triazin-3-yl)thio]methyl}-3-cephem-4-carboxylic acid disodium salt hemiheptahydrate. Essay (HPLC)=99.5%. Yield 85.1%.

We claim:

1. A process for preparing disodium 7-{[2-(2-aminothiazol-4-yl)-2-syn-methoxyimino]acetamido}-3-{[(2,5-dihydro-6-hydroxy-2-methyl-5-oxo-1,2,4-triazin-3-yl)thio]methyl}-3-cephem-4-carboxylate hemiheptahydrate, which comprises reacting 7-amino-3-(2,5-dihydro-6-hydroxy-2-methyl-5-oxo-1,2,4-triazin-3-yl)thiomethyl-3-cephem-4-carboxylate with 2-mercaptobenzothiazole 2-(2-aminothiazol-4-yl)-2-syn-methoxyiminoacetate in an aqueous solution in the presence of an organic solvent and an amine selected from the group consisting of trimethylamine, triethylamine, 1,4-dimethylpiperazine, N-ethylpiperidine, pyridine and dimethylaminopyridine, at a temperature of from −20° to 30° C. and treating the aqueous solution with a salt of a base selected from the group consisting of dicyclohexylamine, diphenylamine, diisopropylamine, N-tert-butylcyclohexylamine and N,N-dibenzylethylenediamine, to form a precipitate; and reacting the precipitate with aqueous sodium 2-ethylhexanoate in the presence of an organic solvent.

2. A process for preparing disodium 7-{[2-(2-aminothiazol-4-yl)-2-syn-methoxyimino]acetamido}-3-{[(2,5-dihydro-6-hydroxy-2-methyl-5-oxo-1,2,4-triazin-3-yl)thio]methyl}-3-cephem-4-carboxylate hemiheptahydrate, which comprises reacting 7-amino-3-(2,5-dihydro-6-hydroxy-2-methyl-5-oxo-1,2,4-triazin-3-yl)thiomethyl-3-cephem-4-carboxylate with 2-mercaptobenzothiazole 2-(2-aminothiazol-4-yl)-2-syn-methoxyimino-acetate in an aqueous solution in the presence of an organic solvent and triethylamine at a temperature of from −20° to 30° C.; treating the aqueous solution with N,N-dibenzylethylenediamine acetate to form a precipitate; and reacting the precipitate with aqueous sodium 2-ethylhexanoate in the presence of an organic solvent.

3. A process for preparing disodium 7-{[2-(2-aminothiazol-4-yl)-2-syn-methoxyimino]acetamido}-3-{[(2,5-dihydro-6-hydroxy-2-methyl-5-oxo-1,2,4-triazin-3-yl)thio]methyl}-3-cephem-4-carboxylate hemiheptahydrate, which comprises reacting N,N-dibenzylethylenediamine {[(2,5-dihydro-6-hydroxy-2-methyl-5-oxo-1,2,4-triazin-3-yl)thio]methyl}-3-cephem-4-carboxylate with aqueous sodium 2-ethylhexanoate in the presence of an organic solvent.

* * * * *

UNITED STATES PATENT AND TRADEMARK OFFICE
CERTIFICATE OF CORRECTION

PATENT NO. : 5,026,843

DATED : June 25, 1991

INVENTOR(S) : MONGUZZI et al

Page 1 of 2

It is certified that error appears in the above-identified patent and that said Letters Patent is hereby corrected as shown below:

On the title page, item [75], the names of the inventors should be REVERSED as follows: (1) Riccardo MONGUZZI; (2) Silvano MENAPACE; and (3) Piergiorgio ANZAGHI. Please also note that the second inventor's last name has been misspelled, delete "Menaspace" and insert therefor --MENAPACE--.

Column 3, line 18, delete "tetrahydofuran" and insert therefor --tetrahydrofuran--.

Column 4, line 41, delete "carboxylate" and insert therefor --carboxylic acid--;

line 61, delete "carboxylate" and insert therefor --carboxylic acid--.

UNITED STATES PATENT AND TRADEMARK OFFICE
CERTIFICATE OF CORRECTION

PATENT NO. : 5,026,843

DATED : June 25, 1991

INVENTOR(S) : Monguzzi, et al

It is certified that error appears in the above-identified patent and that said Letters Patent is hereby corrected as shown below:

Column 2, formula IV, that portion of the formula reading

" $\xrightarrow{THF/H_2O}_{TEA}$ " should read -- a) $\xrightarrow{THF/H_2O}_{TEA}$ --;

formula III, that portion of the formula reading

" $\xrightarrow{DEBD.2CH_3COOH}$ " should read -- b) $\xrightarrow{DEBD.2CH_3COOH}$ --;

formula II, that portion of the formula reading

" $+NH_2-CH_2-C_6H \xrightarrow{EEsNa}$ "

should read -- $+NH_2-CH_2-C_6H_5$ c) $\xrightarrow{EEsNa}$ --.

Signed and Sealed this

Nineteenth Day of January, 1993

*Attest:*

DOUGLAS B. COMER

*Attesting Officer*     *Acting Commissioner of Patents and Trademarks*